United States Patent [19]

Ibi et al.

[11] Patent Number: 4,978,754

[45] Date of Patent: Dec. 18, 1990

[54] PREPARATION PROCESS OF UNSATURATED CARBOXYLIC ACID AMIDE

[75] Inventors: Akira Ibi; Masanori Kitagawa, both of Mobara; Eiichi Sagawa, Chiba; Koichi Takeuchi, Mobara; Etsuo Ohkawado, Kamakura, all of Japan

[73] Assignee: Mitsui Toatsu Chemicals, Incorporated, Tokyo, Japan

[21] Appl. No.: 282,687

[22] Filed: Dec. 12, 1988

[30] Foreign Application Priority Data

Dec. 17, 1987 [JP] Japan ................................ 62-317450
Aug. 5, 1988 [JP] Japan ................................ 63-194535

[51] Int. Cl.[5] .......................................... C07D 295/023

[52] U.S. Cl. .................................... 544/176; 544/386; 546/245; 548/538

[58] Field of Search ................ 564/136; 544/386, 176; 548/538; 546/245

[56] References Cited

U.S. PATENT DOCUMENTS 2,702,822 2/1955 Weisgerber ......................... 564/205
3,914,303 10/1975 Daniher .............................. 564/136

*Primary Examiner*—Robert A. Wax
*Assistant Examiner*—Frederick F. Tsung
*Attorney, Agent, or Firm*—Fisher, Christen & Sabol

[57] ABSTRACT

A process for the preparation of an N-substituted unsaturated carboxylic acid amide represented by the following formula:

$$CH_2{=}\overset{R^1}{\overset{|}{C}}CON\begin{matrix} / (CH_2)_m \backslash \\ \backslash (CH_2)_n / \end{matrix}Y$$

wherein $R^1$ means a hydrogen atom or methyl group Y denotes a methylene group, oxygen atom or methylimino group, m and n stand individually for an integer of 0 to 5, and m+n is an integer of 3 to 5. The process comprises reacting a specified $\beta$-alkoxy-substituted carboxylate with a specified cyclic amine to form a $\beta$-alkoxy-substituted carboxylic acid amide compound and then removing an alcohol from the carboxylic acid amide compound in the presence of a basic catalyst to form an unsaturated group.

17 Claims, No Drawings

PREPARATION PROCESS OF UNSATURATED CARBOXYLIC ACID AMIDE

BACKGROUND OF THE INVENTION

1. Field of the Invention

This invention relates to an improved process for the preparation of an N-substituted unsaturated carboxylic acid amide (hereinafter called "N-substituted amide") represented by the following formula (A):

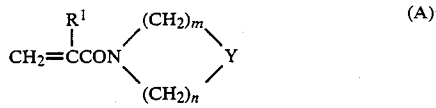

wherein $R^1$ means a hydrogen atom or methyl group, Y denotes a methylene group, oxygen atom or methylimino group, m and n stand individually for an integer of 0 to 5, and m+n is an integer of 3 to 5.

2. Description of the Related Art

The above-described N-substituted amides are useful compounds having a wide variety of utility, such as, water-absorbing agents, non-fogging agents, condensation preventives, isolation membranes, resin modifiers, etc.

An N-substituted amide can generally be prepared by aminolysis of an unsaturated carboxylic acid ester with an amino compound. Michael addition, however, takes place to the double bond of the amino compound upon aminolysis of the unsaturated carboxylic acid ester with amino compound, so that the selectivity to the intended product is low. Reformation of a double bond from the Michael addition product requires a step such that pyrolysis is effected at a temperature as high as 180° to 300° C. so as to release the amino compound thus added. Side reactions such as formation of polymers take place in the step, whereby the yield of the intended product is lowered significantly (Japanese Laid-Open Patent Application No. 111016/1975).

In order to suppress these side reactions, it has been proposed to obtain an intended product by first of all adding a lower alcohol to each double bond, conducting aminolysis and then effecting de-alcoholization at an elevated temperature to re-form the double bond again (Japanese Laid-Open Patent Application No. 66623/1974; U.S. Pat. Nos. 2,534,585; 2,702,822). Although the above method is effective for the objective of preventing Michael addition of the amino compound to the double bond, it is accompanied by a drawback that side reactions, such as, polymerization, take place upon re-formation of the double bond by the de-alcoholization reaction and the yield of the intended product is hence reduced.

As a method for protecting a double bond, it has been known to add cyclopentadiene to the double bond by a Diels-Alder reaction. After completion of aminolysis, the cyclopentadiene is removed by pyrolysis (Japanese Laid-Open Patent Application No. 66625/1974, etc.). Formation of byproducts still cannot be avoided even by this method. Further, this method requires steps for the separation and recovery of the removed cyclopentadiene from the intended product. Moreover, it is impossible to completely avoid admixture of a trace amount of cyclopentadiene into the final product.

SUMMARY OF THE INVENTION

An object of this invention is to provide a process for the preparation of an N-substituted amide while minimizing the formation of byproducts.

Another object of this invention is to provide a process for the preparation of a high-purity N-substituted amide in a high yield.

The present inventors have conducted an extensive investigation with a view toward developing a process which may be able to provide an N-substituted amide in a high yield without byproducts.

As a result, it has been found that an N-substituted amide of high purity can be prepared in a high yield with suppressed formation of byproducts by reacting a $\beta$-alkoxy-substituted carboxylate represented by the following formula (B):

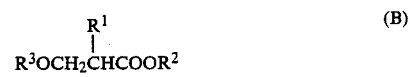

wherein $R^1$ has the same meaning as defined in the formula (A) and $R^2$ and $R^3$ mean independently an alkyl group having 1 to 3 carbon atoms (hereinafter called "$\beta$-alkoxy-substituted carboxylate") with a cyclic amine represented by the following formula (C):

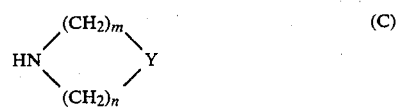

wherein Y, m and n have the same meanings as defined in the formula (A) (hereinafter called "cyclic amine") and then removing an alcohol under mild conditions in the presence of a catalyst to form a double bond.

DETAILED DESCRIPTION OF THE INVENTION

The present invention includes the following processes.

A process for the preparation of an unsaturated carboxylic acid amide represented by the following formula (I):

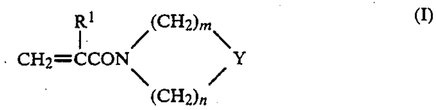

wherein $R^1$ means a hydrogen atom or methyl group, Y denotes an oxygen atom or methylimino group, m and n stand individually for an integer of 0 to 5, and m+n is an integer of 3 to 5, which comprises reacting a $\beta$-alkoxy-substituted carboxylate represented by the following formula (II):

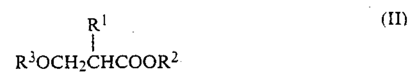

wherein $R^1$ has the same meaning as defined above and $R^2$ and $R^3$ mean independently an alkyl group having 1 to 3 carbon atoms with a cyclic amine represented by the following formula (III):

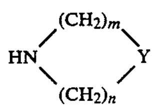

wherein Y, m and n have the same meanings as defined above to form a β-alkoxy-substituted carboxylic acid amide compound and then removing an alcohol from the carboxylic acid amide compound in the presence of a basic catalyst to form an unsaturated group.

A process for the preparation of an unsaturated carboxylic acid amide represented by the following formula (V):

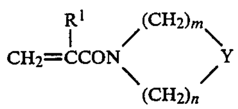

wherein $R^1$ means a hydrogen atom or methyl group, Y denotes a methylene group, and m+n is an integer of 3 to 5, which comprises reacting a β-alkoxy-substituted carboxylate represented by the following formula (II):

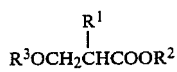

wherein $R^1$ has the same meaning as defined above and $R^2$ and $R^3$ mean independently an alkyl group having 1 to 3 carbon atoms with a cyclic amine represented by the following formula (IV):

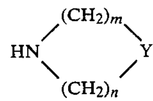

wherein Y, m and n have the same meanings as defined above to synthesize a β-alkoxy-substituted carboxylic acid amide compound and then removing an alcohol from the carboxylic acid amide compound in the presence of a basic catalyst to form an unsaturated group.

A process for the preparation of an unsaturated carboxylic acid amide represented by the following formula (V):

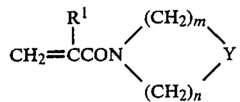

wherein $R^1$ means a hydrogen atom or methyl group, Y denotes a methylene group, and m+n is an integer of 3 to 5, which comprises reacting a β-methoxy-substituted carboxylate represented by the following formula (VI):

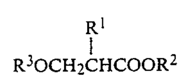

wherein $R^1$ has the same meaning as defined above and $R^2$ means an alkyl group having 1 to 3 carbon atoms with a cyclic amine represented by the following formula (V):

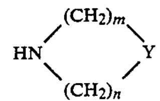

wherein Y, m and n have the same meanings as defined above to synthesize a β-methoxy-substituted carboxylic acid amide compound and then removing methanol from the carboxylic acid amide compound in the presence of an alkali metal alcoholate catalyst represented by the following formula (VII):

$$R^4OM \quad \text{(VII)}$$

wherein $R^4$ means a methyl or ethyl group and M denotes an alkali metal selected from sodium or potassium, thereby forming an unsaturated group.

Preferred embodiments of this invention are hereinafter described.

Illustrative examples of the β-alkoxy-substituted carboxylate employed in this invention, include methyl β-methoxypropionate, ethyl β-methoxypropionate, n-propyl β-methoxypropionate, isopropyl β-methoxypropionate, methyl β-methoxyisobutyrate, ethyl β-methoxyisobutyrate, n-propyl β-methoxyisobutyrate, isopropyl β-methoxyisobutyrate, methyl β-ethoxypropionate, ethyl β-ethoxypropionate, n-propyl β-ethoxypropionate, isopropyl β-ethoxypropionate, methyl β-ethoxyisobutyrate, ethyl β-ethoxyisobutyrate, n-propyl β-ethoxyisobutyrate, isopropyl β-ethoxyisobutyrate, methyl β-isopropoxypropionate, ethyl β-isopropoxypropionate, n-propyl β-isopropoxypropionate, isopropyl β-isopropoxypropionate, methyl β-isopropoxyisobutyrate, ethyl β-isopropoxyisobutyrate, n-propyl β-isopropoxyisobutyrate, isopropyl β-isopropoxyisobutyrate, methyl β-n-propoxypropionate, ethyl β-n-propoxypropionate, n-propyl β-n-propoxypropionate, isopropyl β-n-propoxypropionate, methyl β-n-propoxyisobutyrate, ethyl β-n-propoxyisobutyrate, n-propyl β-n-propoxyisobutyrate, isopropyl β-n-propoxyisobutyrate, etc. Each of these alkyl alkoxy-substituted carboxylates can be obtained by adding its corresponding alcohol to the double bond of its corresponding acrylate or methacrylate.

Exemplary cyclic amines include pyrrolidine, piperidine, hexamethyleneimine, morpholine, N-methyl-piperazine, and the like.

In the present invention, a β-alkoxy-substituted carboxylic acid amide is obtained first of all by aminolysis of its corresponding β-alkoxy-substituted carboxylate with cyclic amine. It is preferred to charge 0.3 to 3 moles of the cyclic amine per mole of the β-alkoxy-substituted carboxylate.

The reaction pressure can preferably be atomospheric pressure or reduced pressure. The desirable reaction pressure ranges from 50 to 760 mmHg.

The reaction temperature should be at least the boiling point of the byproduced alcohol. Desirably, a temperature of 40° to 180° C. is desired although it varies depending upon the reaction pressure. For increased reaction velocity and conversion, it is advantageous to proceed with the aminolysis while distilling out the byproduced alcohol from the reaction system. Although the reaction proceeds without any catalyst since the cyclic amine is basic, it is feasible to add a known basic aminolysis catalyst, for example, sodium methoxlde or sodium amide.

Although the thus-obtained β-alkoxy-substituted carboxylic acid amide can be purified by distillation under reduced pressure for use in the next step, it is usable for the next reaction by simply distilling out unreacted raw materials and low boiling-point byproducts after completion of the reaction.

Next, an alcohol is removed from the β-alkoxy-substituted carboxylic acid amide to synthesize an N-substituted amide. If the intended product is prepared by cracking at an elevated temperature, has been practiced conventionally, lots of undesirable byproducts such as polymers are formed so that the purification of the intended product is rendered complex and its yield is lowered significantly. It is, therefore essential, to remove the alcohol under mild conditions in the presence of a catalyst in this invention. A basic catalyst is used as the catalyst.

Illustrative examples of the basic catalyst useful in this invention include alkali metal alcoholates, alkali metal hydroxides, alkaline earth metal hydroxides, alkaline earth metal oxides, alkali metal carbonates, etc.

Examples of alkali metal alcoholates, include sodium methylate, sodium ethylate, potassium methylate, potassium ethylate and the like.

Examples of alkali metal hydroxides, include lithium hydroxide, sodium hydroxide, potassium hydroxide, rubidium hydroxide, cesium hydroxide, etc. On the other hand, alkaline earth metal hydroxides include magnesium hydroxide, calcium hydroxide, strontium hydroxide and barium hydroxide by way of example. Examples of alkaline earth metal oxides, include magnesium oxide, calcium oxide, barium oxide and so on.

Examples of exemplary alkali metal carbonates, include sodium carbonate and potassium carbonate. These basic catalysts can each be added to the reaction system as a solution dissolved in an inert solvent or as is, namely, as a solid.

It is preferable to conduct the reaction at a low temperature in order to suppress side reactions. The preferable reaction temperature ranges from 50° C. to 170° C. The reaction pressure can suitably be 50 to 760 mmHg. From the standpoint of increase of the reaction velocity, it is desirable to proceed with the reaction while distilling off the resulting alcohol.

It is also feasible to use a solvent as another means for preventing side reactions. Although use of a solvent is not essential in this invention, the yield of the reaction product is not lowered by the use of a solvent and can still be maintained at a high level. Illustrative examples of the solvent include N,N-dimethylformamide, N,N-dimethylacetamide, N,N-dimethylsulfoxide, toluene and xylene.

After completion of the reaction, the basic catalyst is neutralized with a mineral acid such as hydrochloric acid or sulfuric acid or an organic acid such as acetic acid, and the waste catalyst is removed by extraction, or the insoluble catalyst is removed by filtration or centrifugation. The reaction mixture is then subjected to distillation or the like to purify the intended product.

Incidentally, it is preferable to add a polymerization inhibitor upon conducting the reaction and purification of the intended product. Illustrative examples of the polymerization inhibitor include hydroquinone, hydroquinone monomethyl ether, phenothiazine and cupferron.

This invention is hereinafter described specifically by the following Examples.

EXAMPLE 1

[Aminolysis]

In a four-neck flask which was equipped with a stirrer and a fractional distillation column having a reflux condenser at the top thereof and packed with glass-made Raschig rings, 118.1 g (1.0 mole) of methyl β-methoxypropionate and 142.2 g (2.0 moles) of pyrrolidine were charged. Their reaction was allowed to proceed with at 100° C. while distilling off the resulting methanol. The reaction was brought to completion in 6 hours. After completion of the reaction, unreacted pyrrolidine was distilled off under reduced pressure. Low boiling-point components were distilled off further, whereby 146.0 g of a reaction mixture was obtained. The content of β-methoxypropyloylpyrrolidine in the reaction mixture was 93 percent.

[Removal of alcohol]

The reaction mixture obtained by the above-described aminolysis was placed in a similar reactor as in the above aminolysis, followed by addition of 2.7 g of sodium methylate as a catalyst and 0.3 g of cupferron as a polymerization inhibitor. They were reacted at 120° C. and 300 mmHg. The reaction was allowed to proceed while distilling off the byproduced alcohol from the reaction system. The reaction was brought to completion in 3 hours. The resulting reaction mixture was purified by distillation under reduced pressure to obtain 101.5 g of N-acryloylpyrrolidene. Its purity and yield were 99.8 and 81.1 percent, respectively (based on the methyl β-methoxypropionate charged).

EXAMPLES 2 TO 14

Using a similar reactor as in Example 1 and raw materials and catalysts shown in Table 1, similar aminolysis and de-alcoholization reactions as in Example 1 were separately conducted to synthesize corresponding N-substituted amides. The results are summarized in Table 1.

TABLE 1

| Example | β-Alkoxy-substituted carboxylic acid | (charge in grams) | Cyclic amine compound | (charge in grams) | Catalyst | (charge in grams) | N-Substituted amide | (yield in grams) | Purity (%) | Yield (%) |
|---|---|---|---|---|---|---|---|---|---|---|
| 2 | Methyl β-methoxy-propionate | 118.1 | Pyrrolidine | 142.2 | Calcium hydroxide | 2.7 | N-Acryloyl-pyrrolidine | 110.2 | 99.7 | 88.8 |
| 3 | Methyl β-methoxy-propionate | 118.1 | Piperidine | 170.4 | Sodium methylate | 2.7 | N-Acryloyl-piperidine | 110.3 | 99.5 | 79.6 |
| 4 | Methyl β-methoxy-propionate | 118.1 | Hexamethyl-eneimine | 198.4 | Potassium carbonate | 2.7 | N-Acryloyl-hexamethylene-imine | 115.3 | 99.6 | 75.6 |
| 5 | Methyl β-methoxy-propionate | 118.1 | Pyrrolidine | 142.2 | Lithium hydroxide | 1.8 | N-Acryloyl-pyrrolidine | 100.8 | 99.8 | 80.9 |
| 6 | Methyl β-methoxy-propionate | 118.1 | Morpholine | 174.2 | Calcium hydroxide | 2.7 | N-Acryloyl-morpholine | 98.8 | 99.5 | 70.3 |

TABLE 1-continued

| Example | β-Alkoxy-substituted carboxylic acid | (charge in grams) | Cyclic amine compound | (charge in grams) | Catalyst | (charge in grams) | N-Substituted amide | (yield in grams) | Purity (%) | Yield (%) |
|---|---|---|---|---|---|---|---|---|---|---|
| 7 | Methyl β-methoxy-propionate | 118.1 | N-Methyl-piperazine | 200.3 | Lithium hydroxide | 1.8 | N-Acryloyl-N'-methyl-piperazine | 99.9 | 99.0 | 71.1 |
| 8 | Methyl β-methoxy-isobutyrate | 132.6 | Pyrrolildine | 142.2 | Sodium methylate | 2.7 | N-Methacryloyl-pyrrolidine | 101.2 | 99.7 | 72.9 |
| 9 | Ethyl β-ethoxy-propionate | 146.2 | Pyrrolidine | 142.2 | Calcium hydroxide | 2.7 | N-Acryloyl-pyrrolidine | 106.8 | 99.7 | 85.2 |
| 10 | Ethyl β-ethoxy-isobutyrate | 160.2 | Morpholine | 174.2 | Cesium hydroxide | 2.7 | N-Methacryloyl-morpholine | 115.2 | 99.4 | 75.1 |
| 11 | Methyl β-methoxy-propionate | 118.1 | Pyrrolidine | 142.2 | Potassium methylate | 2.7 | N-Acryloyl-pyrrolidine | 108.8 | 99.8 | 86.9 |
| 12 | Methyl β-methoxy-propionate | 118.1 | Hexamethyl-eneimine | 198.4 | Calcium oxide | 2.7 | N-Acryloyl-hexamethylene-imine | 107.4 | 99.5 | 70.1 |
| 13 | Methyl β-methoxy-isobutyrate | 132.6 | Pyrrolidine | 142.2 | Barium hydroxide | 2.7 | N-Methacryloyl-pyrrolidine | 103.2 | 99.8 | 75.2 |
| 14 | Ethyl β-ethoxy-propionate | 146.2 | Piperidine | 170.4 | Barium hydroxide | 2.7 | N-Acryloyl-piperidine | 107.8 | 99.4 | 78.2 |

According to the process of this invention, N-substituted amides of high purity can be prepared in a high yield while minimizing the formation of by-products such as polymers. The resultant N-substituted amides can provide high molecular-weight polymers suitable for use in application fields such as water-absorbing agents, non-fogging agents, condensation preventives, isolation membranes and resin modifiers by their homopolymerization or their copolymerization with vinyl monomers.

What is claimed is:

1. A process for the preparation of an unsaturated carboxylic acid amide represented by the following formula (I):

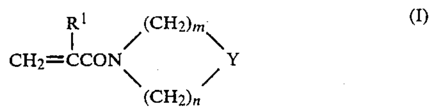

wherein $R^1$ means a hydrogen atom or methyl group, Y denotes an oxygen atom or methylimino group, m and n stand individually for an integer of 0 to 5, and m+n is an integer of 3 to 5, which comprises reacting a β-alkoxy-substituted carboxylate represented by the following formula (II):

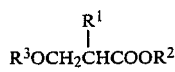

wherein $R^1$ has the same meaning as defined above and $R^2$ and $R^3$ mean independently an alkyl group having 1 to 3 carbon atoms with a cyclic amine represented by the following formula (III):

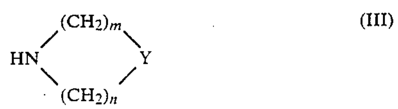

wherein Y, m and n have the same meanings as defined above to form a β-alkoxy-substituted carboxylic acid amide compound and then removing an alcohol from the carboxylic acid amide compound in the liquid phase in the presence of a basic catalyst at a temperature of 50° to 170° C. under a pressure of 50 to 760 mm Hg to form an unsaturated group, wherein the basic catalyst is an alkali metal alcholate, alkalai metal hydroxide, alkaline earth hydroxide alkaline earth metal oxide or alkalai metal carbonate.

2. The process as claimed in claim 1, wherein the cyclic amine is morpholine or N-methylpiperazine.

3. The process as claimed in claim 1, wherein the basic catalyst is sodium methylate, sodium ethylate, potassium methylate or potassium ethylate.

4. The process as claimed in claim 1, wherein the basic catalyst is lithium hydroxide, sodium hydroxide, potassium hydroxide, rubidium hydroxide or cesium hydroxide.

5. The process as claimed in claim 1, wherein the basic catalyst is magnesium hydroxide, calcium hydroxide, strontium hydroxide or barium hydroxide.

6. The process as claimed in claim 1, wherein the basic catalyst is magnesium oxide, calcium oxide or barium oxide.

7. The process as claimed in claim 1, wherein the basic catalyst is sodium carbonate or potassium carbonate.

8. A process for the preparation of an unsaturated carboxylic acid amide represented by the following formula (V):

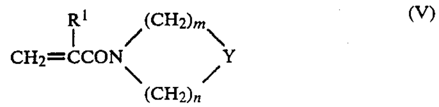

wherein $R^1$ means a hydrogen atom or methyl group, Y denotes a methylene group, and m+n is an integer of 3 to 5, which comprises reacting a β-alkoxy-substituted carboxylate represented by the following formula (II):

$$R^3OCH_2CH(R^1)COOR^2 \quad (II)$$

wherein $R^1$ has the same meaning as defined above and wherein $R^2$ and $R^3$ mean independently an alkyl group having 1 to 3 carbon atoms which a cyclic amine represented by the following formula (IV):

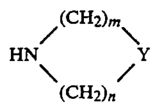

(IV)

wherein Y, m and n have the same meanings as defined above to synthesize a β-alkoxy-substituted carboxylic acid amide compound and then removing an alcohol from the carboxylic acid amide compound in the liquid phase in the presence of a basic catalyst at a temperature of 50° to 170° C. under a pressure of 50 to 760 mm Hg to form an unsaturated group, wherein the basic catalyst is an alkali metal alcholate, alkalai metal hydroxide, alkaline earth hydroxide, alkaline earth metal oxide or alkalai metal carbonate.

9. The process as claimed in claim 8, wherein the cyclic amine is pyrrolidine, piperidine or hexamethyleneimine.

10. The process as claimed in claim 8, wherein $R^3$ is a methyl group in formula (I) and the basic catalyst is lithium hydroxide.

11. The process as claimed in claim 8, wherein the basic catalyst is sodium hydroxide, potassium hydroxide, rubidium hydroxide or cesium hydroxide.

12. The process as claimed in claim 8, wherein the basic catalyst is magnesium hydroxide, calcium hydroxide, strontium hydroxide or barium hydroxide.

13. The process as claimed in claim 8, wherein the basic catalyst is magnesium oxide, calcium oxide or barium oxide.

14. The process as claimed in claim 8, wherein the basic catalyst is sodium carbonate or potassium carbonate.

15. A process for the preparation of an unsaturated carboxylic acid amide represented by the following formula (V):

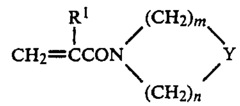

(V)

wherein $R^1$ means a hydrogen atom or methyl group, Y denotes a methylene group, and m+n is an integer of 3 to 5, which comprises reacting a β-methoxy-substituted carboxylate represented by the following formula (VI):

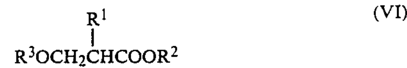

(VI)

wherein $R^1$ has the same meaning as defined above and $R^2$ means an alkyl group having 1 to 3 carbon atoms with a cyclic amine represented by the following formula (IV):

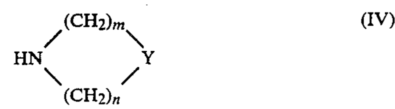

(IV)

wherein Y, m and n have the same meanings as defined above to synthesized a β-methoxy-substituted carboxylic acid amide compound and then removing methanol from the carboxylic acid amide compound in the liquid phase in the presence of an alkali metal alcoholate catalyst represented by the following formula (VII):

$R^4OM$ wherein $R^4$ means a methyl or ethyl group and M denotes an alkali metal selected from sodium or potassium, at a temperature of 50° to 170° C. under a pressure of 50 to 760 mm Hg thereby forming an unsaturated group.

16. The process as claimed in claim 15, wherein the cyclic amine is pyrrolidine, piperidine or hexamethyleneimine.

17. The process as claimed in claim 15, wherein the alkali metal alcoholate is sodium methylate, sodium ethylate, potassium methylate and potassium ethylate.

* * * * *